(12) United States Patent
Chetay et al.

(10) Patent No.: US 7,184,895 B2
(45) Date of Patent: Feb. 27, 2007

(54) METHOD AND SYSTEM OF NON-INTRUSIVELY MONITORING THE MIXTURE RATIO OF A GAS MIXTURE HAVING AT LEAST TWO COMPONENTS

(75) Inventors: Olfa Chetay, Venissieux (FR); Jean-Pierre Dupraz, Lyons (FR); Lionel Lucot, Fleurieux (FR); Didier Taponat, Villeurbanne (FR)

(73) Assignee: Alstom, Paris (FR)

( * ) Notice: Subject to any disclaimer, the term of this patent is extended or adjusted under 35 U.S.C. 154(b) by 0 days.

(21) Appl. No.: 10/038,585

(22) Filed: Jan. 8, 2002

(65) Prior Publication Data
US 2002/0095262 A1    Jul. 18, 2002

(30) Foreign Application Priority Data
Jan. 8, 2001    (FR)    ................... 01 00161

(51) Int. Cl.
*G06F 19/00*    (2006.01)
(52) U.S. Cl. ......................................................... 702/24
(58) Field of Classification Search ................. 702/24; 73/19.12, 23, 24, 861, 53; 123/520; 204/415
See application file for complete search history.

(56) References Cited

U.S. PATENT DOCUMENTS

| | | | |
|---|---|---|---|
| 4,881,412 A | 11/1989 | Northedge | |
| 4,924,701 A * | 5/1990 | Delatorre | ................. 73/152.52 |
| 5,535,632 A * | 7/1996 | Kolpak | .................... 73/861.04 |
| 5,693,873 A | 12/1997 | Thuries et al. | |
| 5,841,020 A * | 11/1998 | Guelich | ...................... 73/19.12 |
| 6,079,217 A | 6/2000 | Judge | |
| 6,272,905 B1 * | 8/2001 | Drzewiecki | ................. 73/53.01 |
| 6,286,360 B1 * | 9/2001 | Drzewiecki | ................. 73/24.01 |
| 6,305,212 B1 * | 10/2001 | Drzewiecki | ................. 73/23.2 |

FOREIGN PATENT DOCUMENTS

| | | |
|---|---|---|
| DE | 42 06 845 A | 9/1993 |
| EP | 0 044 056 A | 1/1982 |
| FR | 2 734 362 A | 11/1996 |

OTHER PUBLICATIONS

Patent Abstracts of Japan, vol. 1998, No. 8, Jun. 30, 1998, & JP 10 068555 A (Mitsubishi Heavy Ind Ltd), Mar. 10, 1998, *abstract.
Guehria, F.M. et al., "Compositional Reservoir Simulation: A New, Efficient, Fully Integrated Solution Technique For The Flow/Thermodynamic Equilibrium Equations", SPE Proceedings, XX, XX, Mar. 20, 1991, pp. 55-68, XP002035429.
Zeisel, D. et al., "A precise and robust quartz sensor based on tuning fork technology for (SF6)-gas density control", Sensors and Actuators A, Elsevier Sequoia S.A., Lausanne, CH, vol. 80, No. 3, Mar. 2000, pp. 233-236, XP004192111, ISSN: 0924-4247.

* cited by examiner

*Primary Examiner*—Michael Nghiem
*Assistant Examiner*—Tung S. Lau
(74) *Attorney, Agent, or Firm*—Sughrue Mion, PLLC

(57) ABSTRACT

A method and system of non-intrusively monitoring the proportion of a component in a gaseous mixture having at least two components and contained in an electrical switchgear enclosure includes measuring the pressure, the temperature, and the density of the gas mixture by using sensors mounted on said enclosure, and in determining said proportion by processing the measured values in a data-processing unit.

17 Claims, 1 Drawing Sheet

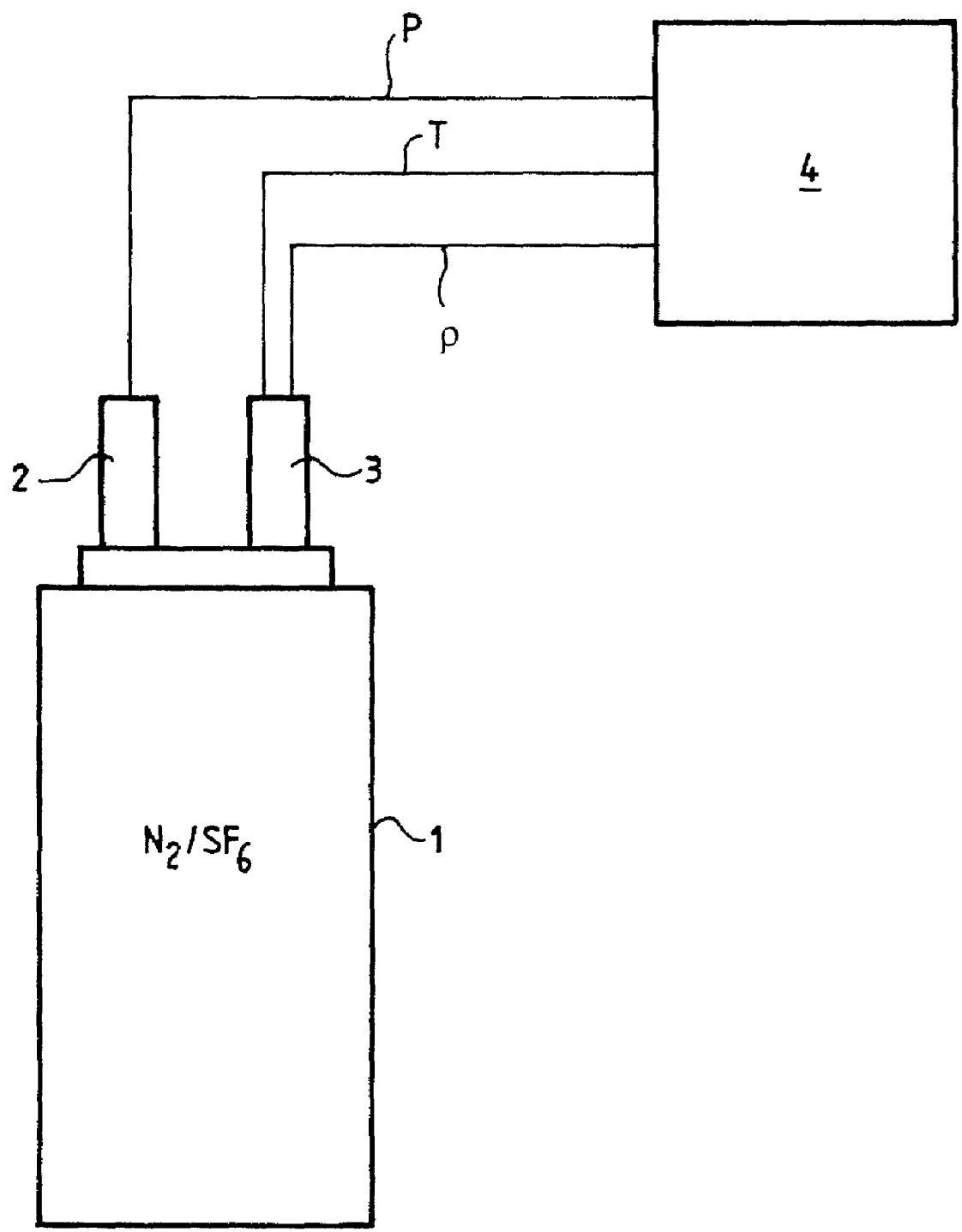

METHOD AND SYSTEM OF NON-INTRUSIVELY MONITORING THE MIXTURE RATIO OF A GAS MIXTURE HAVING AT LEAST TWO COMPONENTS

The invention relates to a method of non-intrusively monitoring the mixture ratio of a gas mixture that has at least two components and that is under a pressure of a few bars inside an enclosure.

The invention relates more particularly to monitoring the insulation gas in gas-insulated high-voltage electrical switchgear.

BACKGROUND OF THE INVENTION

The insulation gas typically used in such switchgear is sulfur hexafluoride ($SF_6$). In order to combat global warming due to greenhouse gas emission, the current trend is to mix the $SF_6$ with some other gas such as nitrogen ($N_2$) or such as carbon fluoride ($CF_4$). That type of two-component mixture also improves the breaking performance of electrical switchgear at very low temperatures ($-50°$ C.). It is possible that mixtures having more than two components might be used in the future.

The ratio of the $SF_6/N_2$ or $SF_6/CF_4$ mixture lies approximately in the range 50/50 to 80/20. To maintain a breaking capacity that is satisfactory in electrical switchgear that is insulated with a gas mixture of the $N_2/SF_6$ or $CF_4/SF_6$ type, it is essential for the proportion of $N_2$ or of $CF_4$ in the gas mixture to remain constant even in the event of leakage. Differential losses between the two components of the mixture can give rise to loss of performance in terms of breaking capacity.

There is also a need for manufacturers of gas-insulated electrical switchgear to specify accurately the ratio of the mixture after filling, in particular in order to satisfy the switchgear rating conditions.

To determine the mixture ratio or else the proportion of one component in a two-component gas mixture, it is known that chromatography or acoustic techniques can be used. However, those methods remain limited to use in the laboratory, and they are not applicable to on-site monitoring of the insulation gas in electrical switchgear. In addition, those methods are "intrusive" because they require the gas mixture to be tapped, which is not compatible with the operating conditions of gas-insulated electrical switchgear.

OBJECTS AND SUMMARY OF THE INVENTION

An object of the invention is thus to provide a solution that is simple, inexpensive, and non-intrusive for accurately monitoring the proportion of one component relative to the other in a gas mixture having at least two components.

More particularly, an object of the invention is to make it possible to monitor accurately the proportion of $N_2$ or of $CF_4$ in an $N_2/SF_6$ or a $CF_4/SF_6$ gas mixture serving as insulation gas for high-voltage switchgear.

The monitoring method of the invention makes use of the equations of thermodynamics in particular to determine the proportion of a component in the mixture. It is known that a mixture which is made up of at least two components that have sufficiently different molecular masses is determined entirely by four magnitudes: temperature, pressure, density, and mixture ratio. Tests have shown that, by using commercially-available industrial sensors to measure temperature, pressure, and density, the mixture ratio can be deduced relatively accurately from the resulting measurements by calculation or by table look-up.

The invention thus provides a method of monitoring the proportion of a component in a gaseous mixture having at least two components and contained in an electrical switchgear enclosure, said method consisting in measuring the pressure, the temperature, and the density of the gas mixture by means of sensors mounted on said enclosure, and in determining said proportion by processing the measured values in a data-processing unit, so as to enable the mixture to be monitored non-intrusively.

A magnitude representative of the density of the gas mixture may be measured by means of a vibrating-blade sensor. This type of sensor has two vibrating blades, one in a vacuum and the other in the gas mixture, and it delivers the difference in vibration frequency between the two blades, this frequency difference being representative of the density of the gas mixture. The density of the gas mixture may also be derived from measuring the permittivity of the gas mixture by means of a capacitor or the like, as is well known to the person skilled in the art. The density of the gas mixture may also be derived from measuring the refractive index of the gas mixture by means of an interferometer or the like.

BRIEF DESCRIPTION OF THE DRAWING

The method of the invention is described below in detail with reference to the sole FIGURE.

The sole FIGURE is a very diagrammatical view showing a system for monitoring an insulation gas mixture having two components, e.g. $N_2/SF_6$, in a gas-insulated high-voltage circuit-breaker, and for continuously monitoring the proportion of $N_2$ in the gas mixture.

MORE DETAILED DESCRIPTION

As shown in the FIGURE, the gastight enclosure 1 formed by the metal-cladding of the high-voltage circuit-breaker is filled with an $N_2/SF_6$ mixture under a pressure of a few bars, and typically in the range 4 bars to 8 bars. A pressure sensor 2 and a density sensor 3 are mounted on the outside wall of the enclosure 1.

The pressure sensor 2 continuously delivers a signal P representative of the absolute pressure of the gas mixture in the enclosure. The density sensor 3 continuously delivers a signal $\rho$ representative of the density of the gas mixture and also a signal T representative of the temperature of the gas mixture.

These three signals are sent to a processing unit 4 which delivers as output the proportion of $N_2$ in the mixture, or in analogous manner the ratio of the mixture.

The mixture ratio, i.e. the ratio between the partial pressures of $N_2$ and of $SF_6$ in the mixture may firstly be determined by solving the thermodynamic state equations of the two components of the mixture (Beattie and Bridgman equations).

If P, T, and $\rho$ are the variables measured by the sensors, and X is the mixture ratio to be determined, the Beattie and Bridgman equations for a two-component mixture give the following relationships:

$$PSF_6 = A1.\rho SF_6 + A2.(\rho SF_6)^2 + A3.(\rho SF_6)^3$$

$$PN_2 = A4.\rho N_2$$

$$P = X\,PN_2 + (1-X).PSF_6$$

$$\rho = \rho N_2 + \rho SF_6$$

where

A1, A2, A3, and A4 are well-known functions of T;

$P\ SF_6$ and $P\ N_2$ are the partial pressures of $N_2$ and of $SF_6$; and $\rho\ N_2$ and $\rho\ SF_6$ are the densities of $N_2$ and of $SF_6$.

On the basis of these equations, the data-processing unit 4 continuously delivers the mixture ratio X as output.

In a variant, the proportion of $N_2$ relative to $SF_6$ in the gas mixture may be obtained on the basis of a data table compiled previously during a test campaign. More particularly, a test volume is filled with a gas mixture whose mixture ratio is known. The temperature of the test volume is caused to vary in stages, e.g. from −40° C. to +60° C. For each stage, the temperature, the pressure, and the density of the mixture are measured, and the resulting three values are recorded in correspondence with the mixture ratio in the table. These operations are repeated for various mixture ratios. The resulting data table is then loaded and stored in a memory in the unit 4 for the purpose of determining the mixture ratio as a function of the three measured magnitudes constituted by temperature, pressure, and density.

As indicated above, it is possible to use a vibrating-blade sensor that measures a physical magnitude representative of the density of the gas mixture. In which case, the temperature can be derived from the pressure sensor because modern industrial sensors for measuring pressure deliver both the temperature and also the pressure of the gas being monitored.

The measurements may advantageously be used in a data-processing system 4 in the form of an optionally portable microcomputer installed permanently or temporarily on the enclosure of the electrical switchgear. The unit 4 may also be an electronic circuit having a microprocessor or a microcontroller and integrated in equipment including one or more sensors. The sensors may be physically separated, or else they may be integrated in a common multi-function measurement instrument. In the figure, the sensor 3 provides both the temperature-sensing function and the density-sensing function.

When the data-processing unit 4 is a portable microcomputer, it may be advantageous for said unit to store a plurality of data tables of the type indicated above, each table being specific to a respective gas mixture. In addition, the unit 4 may advantageously be programmed to run algorithms for correcting errors and drift specific to the sensors.

The method of the invention can thus be implemented with industrial sensors that are commercially available. Such sensors generally offer very good measurement accuracy, typically better than 1%, and therefore the error relating to the mixture ratio can be less than 1%. With the method of the invention, the measurements are taken non-intrusively, without tapping any gas. The method is applicable for a wide temperature range, typically from −50° C. to +90° C., which corresponds to the extreme operating conditions under which certain gas-insulated high-voltage switchgear operates.

Naturally, the method of the invention is applicable for gas mixtures having two components different from $N_2/SF_6$ or from $CF_4/SF_6$ provided that the accuracy of the sensors is chosen appropriately as a function of the differences in the molecular masses of the two components. The invention is also applicable to a gas mixture having more than two different components.

The invention claimed is:

1. A method of monitoring the proportion X of a component in a gaseous mixture, said gaseous mixture having two components, a first component which is $SF_6$ and a second component selected from the group consisting of $N_2$ and $CF_4$, and being contained in an electrical switchgear enclosure, said method comprising the steps of:

a) measuring the pressure P, the temperature T, and the density ρ of the gas mixture contained in the electrical switchgear enclosure by means of sensors mounted on said enclosure, b) determining said proportion X by processing the measured values of pressure P, temperature T and density ρ in a data-processing unit which delivers as output the proportion X determined by solving the following equations:

$$P(SF_6)=A1.\rho(SF_6)+A2.(\rho(SF_6))^2+A3.(\rho(SF_6))^3$$

and $$P(N_2)=A4.\rho(N_2),$$

$$P=X.P(N_2)+(1-X).P(SF_6),$$

$$\rho=\rho(N_2)+\rho(SF_6),$$

or $$P(CF_4)=A4.\rho(CF_4),$$

$$P=X.P(CF_4)+(1-X).P(SF_6),$$

$$\rho=\rho(CF_4)+\rho(SF_6)$$

where A1, A2, A3 and A4 are functions of T, $P(SF_6)$ and $P(N_2$ or $CF_4)$ are the partial pressures of $SF_6$ and ($N_2$ or $CF_4$), $\rho(N_2)$, $\rho(CF_4)$ and $\rho(SF_6)$ are the densities of $N_2$, $CF_4$ and $SF_6$, and wherein step a) is carried out without tapping said gas mixture.

2. The method according to claim 1, in which said electrical switchgear enclosure is a high-voltage switchgear.

3. The method according to claim 1, in which said electrical switchgear enclosure is a gastight enclosure.

4. The method according to claim 1, in which said proportion X of a component in the mixture is determined by the data-processing unit which stores a data table in a memory, said data table containing a plurality of data items representative of various proportions of said component in correspondence with data items representative of various measurements of the pressure P, of the temperature T, and of the density ρ of the gas mixture containing said component.

5. The method according to claim 1, wherein the density is measured by means of a vibrating-blade sensor.

6. The method according to claim 1, wherein the density is measured by means of a capacitor whose capacitance is a function of the permittivity of the gas mixture.

7. The method according to claim 1, wherein the density is measured by means of an interferometer.

8. A method according to claim 1, in which the data-processing unit is a microcomputer.

9. A method according to claim 1, in which the data-processing unit is formed by microprocessors or microcontrollers.

10. Electrical switchgear provided with an enclosure containing a mixture of two dielectric gases under pressure, a first component which is $SF_6$ and a second component selected from the group consisting of $N_2$ or $DF_4$, wherein the proportions of the dielectric gases in the mixture are determined by implementing a method according to claim 1.

11. Electrical switchgear according to claim 10, wherein the electrical switchgear enclosure is a high-voltage switchgear.

12. Electrical switchgear according to claim 10, wherein electrical switchgear enclosure is a gastight enclosure.

13. A method according to claim 1, in which said gaseous mixture acts as an insulation gas in the electrical switchgear.

14. Electrical switchgear provided with an enclosure containing a gaseous mixture of two dielectric gases under pressure, a first component which is $SF_6$ and a second component selected from the group consisting of $N_2$ or $DF_4$, wherein the proportion X of one of these dielectric gases in the mixture is determined by implementing a method comprising the steps of:
  a) measuring the pressure P, the temperature T, and the density ρ of the gas mixture contained in the electrical switchgear enclosure by means of sensors mounted on said enclosure,
  b) determining said proportion X by processing the measured values of pressure P, temperature T and density ρ in a data-processing unit which delivers as output the proportion X determined by solving the following equations:

$$P(SF_6)=A1.\rho(SF_6)+A2.(\rho(SF_6))^2+A3.(\rho(SF_6))^3$$

and $$P(N_2)=A4.\rho(N_2),$$

$$P=X.P(N_2)+(1-X).P(SF_6),$$

$$\rho=\rho(N_2)+\rho(SF_6),$$

or $$P(CF_4)=A4.\rho(CF_4),$$

$$P=X.P(CF_4)+(1-X).P(SF_6),$$

$$\rho=\rho(CF_4)+\rho(SF_6)$$

where A1, A2, A3 and A4 are functions of T,
$P(SF_6)$ and $P(N_2$ or $CF_4)$ are the partial pressures of $SF_6$ and ($N_2$ or $CF_4$),
$\rho(N_2)$, $\rho(CF_4)$ and $\rho(SF_6)$ are the densities of $N_2$, $CF_4$ and $SF_6$,
wherein step a) is carried out without tapping said gas mixture.

15. A method of monitoring the proportion X of a component in a gaseous mixture, said gaseous mixture having at least two components, a first component which is $SF_6$ and a second component selected from the group consisting of $N_2$ or $DF_4$, and being contained in an electrical switchgear enclosure, said method comprising the steps of:
  a) measuring the pressure P, the temperature T, and the density ρ of the gas mixture contained in the electrical switchgear enclosure by means of sensors mounted on said enclosure,
  b) determining said proportion by processing the measured values of pressure P, temperature T and density ρ in a data-processing unit, which delivers as output the proportion X determined by solving the following equations:

$$P(SF_6)=A1.\rho(SF_6)+A2.\rho(\rho(SF_6))^2+A3.(\rho(SF_6))^3$$

and $$P(N_2)=A4.\rho(N_2),$$

$$P=X.P(N_2)+(1-X).P(SF_6),$$

$$\rho=\rho(N_2)+\rho(SF_6),$$

or $$P(CF_4)=A4.\rho(CF_4),$$

$$P=X.P(CF_4)+(1-X).P(SF_6),$$

$$\rho=\rho(CF_4)+\rho(SF_6)$$

where A1, A2, A3 and A4 are functions of T,
$P(SF_6)$ and $P(N_2$ or $CF_4)$ are the partial pressures of $SF_6$ and ($N_2$ or $CF_4$),
$\rho(N_2)$, $\rho(CF_4)$ and $\rho(SF_6)$ are the densities of $N_2$, $CF_4$ and $SF_6$, and
  c) running algorithms in the data-processing unit for correcting errors and drift specific to said sensors,
wherein step a) is carried out without tapping said gas mixture.

16. A system for monitoring the proportion X of a component in a gaseous mixture, said gaseous mixture having two components, a first component which is $SF_6$ and a second component selected from the group consisting of $N_2$ or $DF_4$, and being contained in an electrical switchgear enclosure, said system comprising:
  at least one sensor mounted on said enclosure for measuring the pressure P, the temperature T, and the density ρ of the gas mixture contained in the electrical switchgear enclosure, said sensor measuring without tapping the said gas mixture, and
  a data processing unit for processing the measured values of pressure, temperature and density, the data processing delivering as output the proportion X determined by solving the following equations:

$$P(SF_6)=A1.\rho(SF_6)+A2.(\rho(SF_6))^2+A3.(\rho(SF_6))^3$$

and $$P(N_2)=A4.\rho(N_2),$$

$$P=X.P(N_2)+(1-X).P(SF_6),$$

$$\rho=\rho(N_2)+\rho(SF_6),$$

or $$P(CF_4)=A4.\rho(CF_4),$$

$$P=X.P(CF_4)+(1-X).P(SF_6),$$

$$\rho=\rho(CF_4)+\rho(SF_6)$$

where A1, A2, A3 and A4 are functions of T,
$P(SF_6)$ and $P(N_2$ or $CF_4)$ are the partial pressures of $SF_6$ and ($N_2$ or $CF_4$),
$\rho(N_2)$, $\rho(CF_4)$ and $\rho(SF_6)$ are the densities of $N_2$, $CF_4$ and $SF_6$.

17. A system for monitoring the proportion X of a component in a gaseous mixture, said gaseous mixture having two components, a first component which is $SF_6$ and a second component selected from the group consisting of $N_2$ or $DF_4$, and being contained in an electrical switchgear enclosure, said system comprising:

first means mounted on said enclosure for measuring the pressure P, the temperature T, and the density ρ of the gas mixture contained in the electrical switchgear enclosure, said first means measuring without tapping said gas mixture, and second means for processing the measured values of pressure, temperature and density and delivering as output the proportion X determined by solving the following equations:

$$P(SF_6) = A1 \cdot \rho(SF_6) + A2 \cdot (\rho(SF_6))^2 + A3 \cdot (\rho(SF_6))^3$$

and $$P(N_2) = A4 \cdot \rho(N_2),$$

$$P = X \cdot P(N_2) + (1-X) \cdot P(SF_6),$$

$$\rho = \rho(N_2) + \rho(SF_6),$$

or $$P(CF_4) = A4 \cdot \rho(CF_4),$$

$$P = X \cdot P(CF_4) + (1-X) \cdot P(SF_6),$$

$$\rho = \rho(CF_4) + \rho(SF_6)$$

where A1, A2, A3 and A4 are functions of T,
$P(SF_6)$ and $P(N_2$ or $CF_4)$ are the partial pressures of $SF_6$ and ($N_2$ or $CF_4$),
$\rho(N_2)$, $\rho(CF_4)$ and $\rho(SF_6)$ are the densities of $N_2$, $CF_4$ and $SF_6$.

* * * * *

UNITED STATES PATENT AND TRADEMARK OFFICE
CERTIFICATE OF CORRECTION

PATENT NO. : 7,184,895 B2 Page 1 of 1
APPLICATION NO. : 10/038585
DATED : February 27, 2007
INVENTOR(S) : Olfa Chetay et al.

It is certified that error appears in the above-identified patent and that said Letters Patent is hereby corrected as shown below:

Col. 5, line 4 of Claim 25, please delete "$DF_4$" and insert therefor --$CF_4$--.

Col. 5, line 4 of Claim 28, please delete "$DF_4$" and insert therefor --$CF_4$--.

Col. 5, line 4 of Claim 29, please delete "$DF_4$" and insert therefor --$CF_4$--.

Col. 5, line 4 of Claim 30, please delete "$DF_4$" and insert therefor --$CF_4$--.

Col. 5, line 4 of Claim 31, please delete "$DF_4$" and insert therefor --$CF_4$--.

Signed and Sealed this

Tenth Day of April, 2007

JON W. DUDAS
*Director of the United States Patent and Trademark Office*